US00PP28491P2

(12) United States Plant Patent
Oudolf

(10) Patent No.: US PP28,491 P2
(45) Date of Patent: Oct. 3, 2017

(54) ***MOLINIA* PLANT NAMED 'DARK BEAUTY'**

(50) Latin Name: *Molinia litoralis*
Varietal Denomination: Dark Beauty

(71) Applicant: Green Elite Collection B.V., Lisserbroek (NL)

(72) Inventor: Piet Oudolf, Hummelo (NL)

(73) Assignee: GREEN ELITE COLLECTION BV, Lisserbroek (NL)

( * ) Notice: Subject to any disclaimer, the term of this patent is extended or adjusted under 35 U.S.C. 154(b) by 0 days.

(21) Appl. No.: 14/999,561

(22) Filed: May 26, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Penny J. Aguirre

(57) ABSTRACT

A new cultivar of *Molinia*, 'Dark Beauty', that is characterized by its tall plant height of 220 cm and its flower dark colored spikes that are fine in texture.

1 Drawing Sheet

Botanical classification: *Molinia litoralis.*
Varietal denomination: 'Dark Beauty'.

BACKGROUND OF THE INVENTION

The present invention relates to a new and distinct cultivar of *Molinia litoralis* and will be referred to hereafter by its cultivar name, 'Dark Beauty'. 'Dark Beauty' represents a new cultivar of herbaceous perennial, an ornamental grass grown for landscape use.

The Inventor discovered the new cultivar, 'Dark Beauty', as a chance seedling in the Inventors garden in Hummelo, Netherlands in the summer of 2009. Although the parentage is unknown, *Molinia litoralis* 'Transparent' (not patented) is thought to be a likely parent based on the characteristics of 'Dark Beauty' and its proximity in the same growing area.

Asexual propagation of the new cultivar was first accomplished by division in Hummelo, Netherlands in 2010 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Dark Beauty' as a unique cultivar of *Molinia.*

1. 'Dark Beauty' exhibits a plant height of 220 cm.
2. 'Dark Beauty' exhibits flower spikes that are fine in texture.
3. 'Dark Beauty' exhibits dark colored flower spikes (due to stigmas).

'Dark Beauty' can be most closely compared to cultivars, *Molinia litoralis* 'Transparent' and *Molinia litoralis* 'Skyracer' (not patented). 'Transparent' differs from 'Dark Beauty' in having flower spikes that are lighter in color and a more open plant habit. 'Skyracer' differs from 'Dark Beauty' in having a taller plant height, in having a more upright growth habit and in lacking dark colored flower spikes.

BRIEF DESCRIPTION OF THE DRAWING

The accompanying photograph illustrates the characteristics of 3 year-old plant of 'Dark Beauty' as grown in a garden in Hummelo, Netherlands. The photograph provides a side view of 'Dark Beauty'. The colors in the photographs are as close as possible with the digital photography techniques available, the color values cited in the detailed botanical description accurately describe the colors of the new *Molinia.*

DETAILED BOTANICAL DESCRIPTION

The following is a detailed description of one-year-old plants of the new cultivar as grown in two-gallon containers in Rougemont, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—August to September in The Netherlands.
*Plant type.*—Herbaceous perennial grass.
*Plant habit.*—Low clump of foliage with tall flowering spikes held upright and slightly cascading.
*Height and spread.*—Reached about 220 cm in height and 50 cm in spread.
*Cold hardiness.*—At least in U.S.D.A. Zone 4.
*Diseases.*—No resistance to susceptibility to diseases has been observed.
*Root description.*—Fibrous, fine, 161D in color.
*Propagation.*—Division.
*Growth rate.*—Moderate.

Culm (stem) description:

*General*.—Slightly oval, solid pith, thin but strong, erect.

*Culm number*.—An average of 7 flowering culms and 15 shorter none flowering culms in a 2-gallon container, forming tight clump.

*Culm color*.—144A in summer, 161D in fall and winter.

*Culm size*.—Average of 2 mm in diameter, averaging 90 cm in length from the base to the tip of the flower panicle and an average of 4.5 cm in length on non-flowering culms.

*Culm surface*.—Glabrous.

*Internode length*.—An average of 4 cm.

Foliage description:

*Leaf shape*.—Narrowly lanceolate.

*Leaf division*.—Simple.

*Leaf margin*.—Entire.

*Leaf base*.—Sheathed to base of culm.

*Leave apex*.—Sharply attenuate.

*Leaf venation*.—Parallel, not distinguishable in color from leaf.

*Leaf width*.—Average of 1 cm at widest section.

*Leaf length*.—Blade; an average of 25 cm, sheathed portion; 3 to 15 cm.

*Leaves per culm*.—Average of 4 on flowering culms and 3 on non-flowering culms.

*Leaf surface*.—Glabrous and dull on both surfaces.

*Ligule*.—0.5 mm in width, comprised of a row of dense stiff hairy on inner surface, NN155C in color.

*Leaf color* (*both surfaces*).—Summer; a blend of 138A and 137C, fall and winter; 161D.

Flower description:

*Inflorescence type*.—Airy panicle of racemes at terminus of stem, primarily symmetrical, overall color of the raceme is a blend of 145B and N77A (due to stigmas) in early summer and maturing to 161D in late fall.

*Inflorescence size*.—Panicle; an average of 28 cm in length and 10 cm in width, racemes; an average of 28 cm in length and 10 cm in width.

*Spikelet description*.—Average of 250 per panicle, awnless, glumes; lower glume 2 mm in length and width, upper glume 3 mm in length and 2 mm in width, 145C in color and suffused with N77A, convex, glabrous surface, lemmas; 2, 4 mm in length and 2 mm in width, convex, glabrous surface, a blend of 144C and 145D in color, palea; 5 mm in length and 1.5 mm in width, 145C in color, convex, glabrous surface.

*Spikelet size*.—About 7 mm in length and 2.5 mm in width (excluding reproductive organs).

*Rachis*.—An average of 45 cm from last leaf, panicle portion an average of 27 cm in length and 1 to 2 mm in width with branches an average of 6 cm in length and 0.5 mm in width, glabrous surface, 144A in color, spikelet (pedicel like); an average of 4 nun in length, wiry, 144A in color, slightly pubescent surface, internode length of racemes 7 mm to 2 cm.

Reproductive organs:

*Androecium*.—Anthers; 2, 3 mm in length and 0.5 mm in width, 200A in color, longitudinal dehiscence, very fine filament, pollen; low in quantity, about 155B in color.

*Gynoecium*.—Pistil; 1, 2 plumose stigmas on short, fine styles about 0.3 mm in length and 145D in color, stigma color is 77A (imparting the dark color to the flower spikes), 2 mm in length and 1 mm in width, ovary; 1-locular, superior, elliptic in shape, 1.5 mm in length, 145D in color.

*Caryopsis*.—2 to 3 mm in length and about 1.5 in width, 165C in color.

It is claimed:

1. A new and distinct cultivar of *Molinia* plant named 'Dark Beauty' as herein illustrated and described.

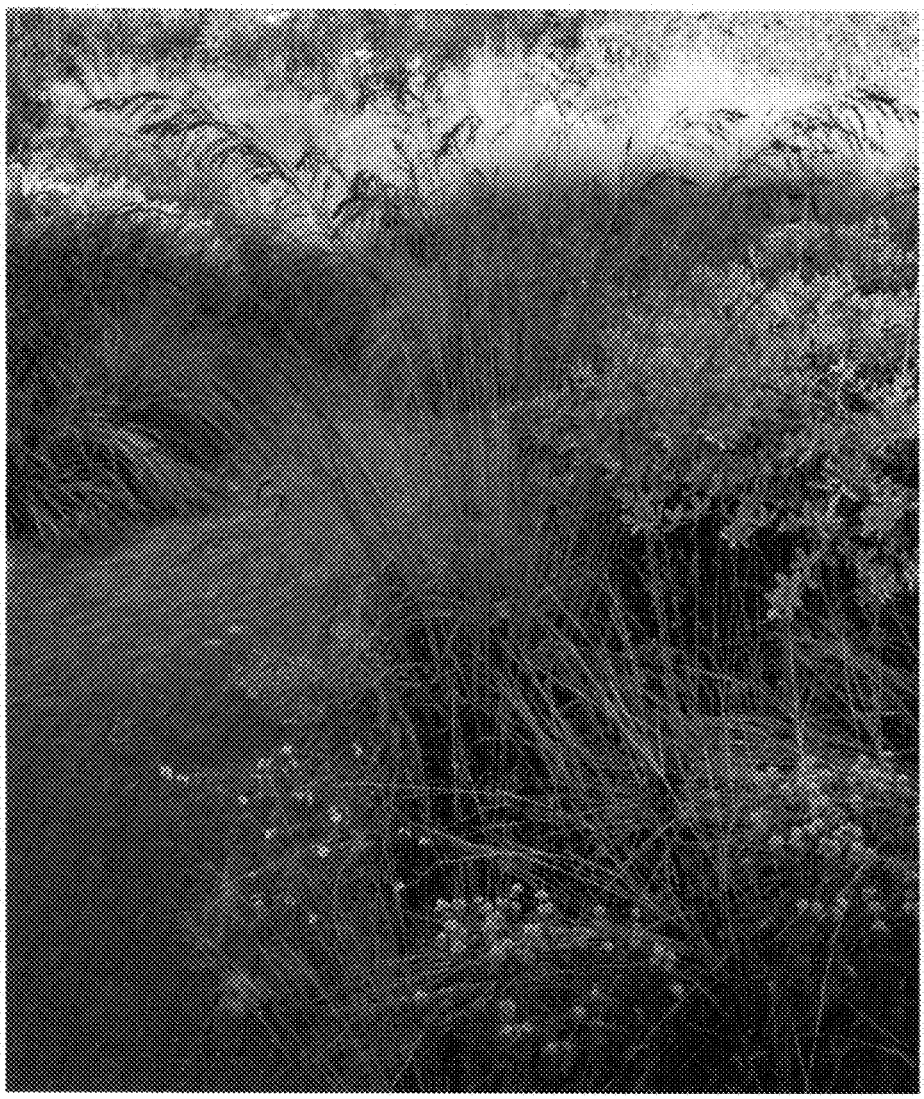

* * * * *